(12) United States Patent
Van de Capelle et al.

(10) Patent No.: US 7,199,903 B2
(45) Date of Patent: Apr. 3, 2007

(54) METHOD AND DEVICE FOR DETERMINING THE COLOR APPEARANCE OF COLOR OVERPRINTS

(75) Inventors: Jean-Pierre Van de Capelle, Rochester, NY (US); Erik Sundermann, Perk (BE); Baldewin Meireson, Zingem (BE); Wim Geurts, Gent (BE)

(73) Assignee: Agfa-Geuaert N.V., Mortsel (BE)

( * ) Notice: Subject to any disclaimer, the term of this patent is extended or adjusted under 35 U.S.C. 154(b) by 991 days.

(21) Appl. No.: 10/143,543

(22) Filed: May 9, 2002

(65) Prior Publication Data

US 2002/0193956 A1 Dec. 19, 2002

Related U.S. Application Data

(63) Continuation-in-part of application No. 09/361,435, filed on Jul. 26, 1999, now Pat. No. 6,483,607, which is a continuation-in-part of application No. 08/824,689, filed on Apr. 8, 1997, now Pat. No. 5,933,578.

(60) Provisional application No. 60/290,147, filed on May 10, 2001.

(51) Int. Cl.
 *G06F 15/00* (2006.01)
 *G06F 15/173* (2006.01)

(52) U.S. Cl. .......................... 358/1.9; 358/1.9; 709/223

(58) Field of Classification Search ................. 358/1.9, 358/518, 523; 709/223, 203; 370/338, 352.4; 347/12, 19, 240
See application file for complete search history.

(56) References Cited

U.S. PATENT DOCUMENTS 5,268,754 A 12/1993 Van de Capelle et al. ............ 358/527

(Continued)

FOREIGN PATENT DOCUMENTS

EP 0586139 8/1993
EP 0622952 4/1994

OTHER PUBLICATIONS

A.U. Agar, "Model Based Color Separation for CMYKcm Printing", *Proceedings of The Ninth IS&T/SID Color Imaging Conference*, pp. 298-302, Scottsdale, AZ, Nov. 5-9, 2001.
Finlayson, G. D., Morovic, P., Crossover Wavelengths of Natural Metamers, in Proceedings of Colour 2000 conference, Derby, UK, Apr. 2000.
Harold Boll, "A Color to Colorant Transformation for a Seven Ink Process," *Proceeding, IS&T's Third Technical Symposium on Proofing and Printing*, pp. 31-35, 1993.

(Continued)

*Primary Examiner*—King Y. Poon
*Assistant Examiner*—Saeid Ebrahimi
(74) *Attorney, Agent, or Firm*—Robert A. Sabourin (57) ABSTRACT

A method and apparatus to predict the color of an overprint of a set of colorants at a set of respective coverage percentages on a substrate of a substrate type using a printing technique. The colorants include some for which a device profile is provided. The method includes determining the colorant parameters of the device profile colorants; determining the spectrum of the substrate, providing spectral colorant parameters for the non-device profile colorants, and determining the color of the overprint. One version including modifying the data of the device profile such that the colorant parameters determined in the step of determining colorant parameters determines the colorant parameters of modified colorants that match the color of the device profile colorants and that cover at least the gamut of the device profile colorants. In one version, the step of determining the determining the color of the overprint includes determining the coverage percentages of the modified colorants corresponding to the colorants of each subset, and using the coverage percentages of the modified colorants to determine the color of the overprint.

4 Claims, 7 Drawing Sheets

U.S. PATENT DOCUMENTS

| | | | | |
|---|---|---|---|---|
| 5,530,656 | A | * | 6/1996 | Six .............................. 702/108 |
| 5,650,942 | A | | 7/1997 | Granger ...................... 364/526 |
| 5,689,349 | A | | 11/1997 | Plettinck et al. ............ 358/500 |
| 5,734,800 | A | | 3/1998 | Herbert et al. ............... 395/109 |
| 5,870,530 | A | | 2/1999 | Balasubramanian ........ 395/109 |
| 5,892,891 | A | | 4/1999 | Dalal et al. ................... 395/109 |
| 5,933,578 | A | * | 8/1999 | Van de Capelle et al. ... 358/1.9 |
| 5,991,511 | A | | 11/1999 | Granger ...................... 395/109 |
| 6,262,744 | B1 | | 7/2001 | Carrein ....................... 345/431 |
| 6,307,645 | B1 | | 10/2001 | Mantell et al. .............. 358/1.9 |
| 6,335,800 | B1 | | 1/2002 | Balasubramanian ........ 358/1.9 |
| 6,335,983 | B1 | | 1/2002 | McCarthy et al. .......... 382/162 |
| 6,373,580 | B1 | | 4/2002 | Walker ....................... 358/1.1 |

OTHER PUBLICATIONS

J. Morovic, M. R. Luo, "A Universal Algorithm for Colour Gamut Mapping", Presented at the Colour Imaging in Multimedia conference, Derby, UK, 1998.

J. S. Arney, Charles D. Arney, and Peter G. Engeldrum, "Modeling the Yule-Nielsen Halftone Effect," *Journal of imaging science and technology,* vol. 40, p. 233, 1996.

J.P. Van de Capelle, "Trade-offs between fundamental and pragmatic colour management systems," *Proceedings, Colour Image Science 2000 (CIS' 2000),* Derby, UK, pp. 127-136, Apr. 2000.

Nobbs, James H.: "Kubelka-Munk Theory and the Prediction of Relectance", Rev. Prog. Coloration, vol. 15, pp. 66-75, 1985.

Jon Y. Hardeberg, "Acquisition and reproduction of colour images: colorimatric and multispectral approaches," *Thesis,* Docteur de L"ecole Nationale Supérieure des Télécommunications, Paris, France, Jan. 1999.

K. Schlaepfer, "The Colour Gamut of the Seven-Colour Printing Process," *Journal of Prepress and Printing Technology,* pp. 22-29, 1997.

M. Mahy and P. Delabastita, "Inversion of the Neugebauer Equations," *Color Research And Applications,* vol. 21, No. 6, pp. 365-374, 1996.

M. Mahy, "Calculation of Color Gamuts Based on the Neugebauer Model," *Color Research and Applications,* vol. 22, No. 6, pp. 404-411, 1997.

M.R. Pointer, "The Gamut of Real Surface Colors," *Color Research and Applications,* vol. 5, No. 3, pp. 145-155, 1980.

Patrick Emmel, Roger David Hersch , "Spectral Colour Prediction Model for Transparent Fluorescent Inks on Paper", *Proceedings of the IS&T/SID 6th Color Imaging Conference: Color Science, Systems, and Applications,* Nov. 17-20, 1998, Scottsdale, Arizona, USA, pp. 116-122.

Jan Morovic, "To Develop a Universal Gamut Mapping Algorithm," *Thesis,* University of Derby, England, Oct. 1998.

B. Meireson and J.P. Van De Capelle, "A New Method For Characterizing Output Devices and Its Fit Into ICC and HIFI Color Workflows", Proc. of the Fifth IS&T/SID Color Imaging Conference , Nov. 1997, Scottsdale, AZ, pp. 66-69.

P. Emmel, Roger David Hersch, "A Model for Colour Prediction of Halftoned Samples Incorporating Light Scattering and Ink Spreading", Proceedings of the IS&T/SID 7th Color Imaging Conference: Color Science, Systems and Applications, pp. 173-181, Nov. 16-19, 1999, Scottsdale, Arizona, USA.

T. J. Cholewo and S. Love, "Gamut boundary determination using alpha-shapes," in Proceedings of the 7th Color Imaging Conference, (Scottsdale, Ariz.), pp. 200-204, Nov. 1999.

P. Emmel, Isaac Amidror, V. Ostromoukhov, Roger David Hersch, "Predicting the Spectral Behaviour of Colour Printers for Transparent Inks on Transparent Support", in Proceedings of the IS &T/SID 96 Color Imaging Conference: Color Science, Systems and Applications, Nov. 19-22, 1996 Scottsdale, Arizona, USA, pp. 86-91.

E. J. Stollnitz, V. Ostromoukhov, David H. Salesin, "Reproducing Color Images Using Custom Inks", in Proceedings of SIGGRAPH 98, in *Computer Graphics Proceedings,* Annual Conference Series, pp. 267-274, 1998.

\* cited by examiner

METHOD AND DEVICE FOR DETERMINING THE COLOR APPEARANCE OF COLOR OVERPRINTS

RELATED PATENT APPLICATIONS

The present invention claims benefit of U.S. Provisional Patent Application Ser. No. 60/290,147 filed May 10, 2001 to inventors Van de Capelle, et al. and titled METHOD AND DEVICE FOR DETERMINING THE COLOR APPEARANCE OF COLOR OVERPRINTS, U.S. application Ser. No. 60/290,147 is herein by reference.

The present application is a continuation-in-part of U.S. Pat. application Ser. No. 09/361,435 to inventors Van de Capelle, et al., titled METHOD AND DEVICE FOR DETERMINING THE COLOR APPEARANCE OF COLOR OVERPRINTS, filed Jul. 26, 1999 now U.S. Pat. No. 6,483,607, U.S. Pat. application Ser. No. 09/361,435 is a continuation in part of application Ser. No. 08/824,689, filed Apr. 8,1997, now U.S. Pat. No. 5,933,578 to inventors Van de Capelle, et al., titled METHOD AND DEVICE FOR DETERMINING THE COLOR APPEARANCE OF COLOR OVERPRINTS. U.S. Pat. application Ser. No. 09/361,435 and U.S. Pat. No. 5,933,578 are referred to herein as the "Parent Patents." Each of U.S. Pat. application Ser. No. 09/361,435 and U.S. Pat. No. 5,933,578 are hereby incorporated herein by reference.

FIELD OF THE INVENTION

The present invention relates to computerized color graphics, color reproduction, and electronic printing systems. In particular, the present invention relates to a method and apparatus for characterizing colorants such as inks and to a method and apparatus for predicting the color appearance of placing one or more colorant layers on top of a substrate such as paper or film as occurs, for example, in printing a page or in photography.

BACKGROUND OF THE INVENTION

Computerized color graphics systems and electronic printing systems are known in the art. Typically, they enable a user to produce a color image—any visual two-dimensional pattern including one or more text, graphic line art elements, continuous tone image elements, and so forth—and from that image to produce a representation that can be printed using a color reproduction system, for example, by producing color separation plates for offset printing. There has been much effort in the past to develop ways to accurately predict the appearance of such an image when printed on a substrate, for example on paper or film, using a number of colorants, such as inks, the prediction carried out without actually printing the image. Similarly, there has been effort to simulate the appearance of such an image without printing the image.

It is desirable to be able to calculate accurately how a picture will look when one prints an image, including a halftoned continuous tone color image, with a certain printing technique on some certain type of substrate using a certain set of colorants (e.g., inks). A method of predicting the color appearance can be used for example to display a simulation of the color appearance on a computer display, or to print a simulation of the color appearance on a more easily accessible and cheaper printer as a proof of what is to be printed finally in production.

It is desirable to do this for both reflection printing on an opaque substrate, and transmission imaging on a transparent substrate.

In order to so predict the appearance of overprints, it is advantageous to spectrally characterizing colorants by parameters that are substantially invariant for all substrates of the same type, and independent of the substrate color, in that, when there is no interaction between colorant layers, one can treat a substrate with one or more colorant overprints on it as a raw colored substrate of the same type but a different color, that different color dependent on the one or more colorant overprints.

The Parent Patents define such colorant parameters and further provide a method for determining the colorant parameters by carrying out some experiments. The colorant parameters are applicable for printing colorants on top of each other with halftoning. The Parent Patents further describe how to determine the spectrum of an overprint of halftoned colorants using the colorant parameters, and also how to obtain the color of an overprint in some color coordinate system, e.g., a device independent color coordinate system such as CIE Lab.

The use of these parameters is described in U.S. Pat. No. 5,933,578 for cases that include when there is little or no interaction between the layers. The method and apparatus of U.S. application Ser. No. 09/361,435 are applicable in cases that include when the colorant parameters of one colorant may be influenced by the other colorants being printed.

Although the methods of the Parent Patents are suited to predicting the overprints of colorants using some spectral colorant parameters, there is still room for improvement. A printing device is often characterized by a device profile. Modem color management techniques such as COLORSYNC™ (Apple Computer, Inc., Cupertino, Calif.) and the methods promoted by the International Color Consortium (ICC, see http://www.color.org) use such profile. A popular profile format is the ICC profile. Such device profiles includes a lookup table providing mapping between some overprint values and colors in some device independent space, e.g., CIE Lab. The normal use of an output table is with multidimensional interpolation to determine the colorant values for some given color specified in the device independent space. ICC profiles do not typically contain any spectral data or any spectral colorant parameters. They are however common in industry, that is, they are often used to predict the color rendition of CMYK printing devices.

It is often required in a job to not only use CMYK colorants, but also to overprint some other colorants, such as PANTONE® colorants or other special inks. Such occurs, for example, in packaging, where logos or items of linework are combined with continuous tone images. The logos or linework elements are often printed in PANTONE® inks and the CT images are mostly printed with CMYK inks. Since overprints of the special ink with any of the CMYK inks have not been measured, there is a problem to determine the color of such overprints. A typical device profile is specified for determining predicting the color of the CMYK parts in a job. There is presently no suitable method for using the profile for determining the color of the overprints of the CMYK of the profile with additional inks.

A first possible solution to this problem is to use a model such as determining the colorant parameters of the Parent Patents. However since the colorant parameters of the CMYK inks are not present in the device profile we have to use some colorant parameters of some CMYK inks, known in the Color Management System. Usually these inks are quite different from the inks of the device profile. This leads to very inconsistent or unstable behavior in the Color Management Systems, since for instance a color consisting of any combination of CMYK will be predicted using the device profile, whereas a color consisting of for instance cyan (C) and a certain percentage (even if this is only 1%) of a special ink will be predicted using some colorant parameters for some cyan ink known in the system and the colorant parameters of the special ink. This may cause the CMS to behave in an unstable manner, because the two colors are calculated using a different path and the result of both paths can be quite far from one another, even if no special ink is involved in the calculations. One aspect of the invention aspect is dealing with the inconsistency issue and stability issue. Another aspect of the present invention is providing device profiles, such as ICC profiles, using the colorant parameters as have been described in one or both of the Parent Patents.

A second possible solution to the described problem, which would not exhibit this unstable behavior, is to make a prediction of the overprinting color by applying a mixing formula in for instance a CMYK, CIE related or RGB color space. With such a method, the color of the cyan would be predicted using the device profile, the color of the special ink would be predicted using its colorant parameters, as if it would not be printed in combination with the cyan, and the color of the overprint would be predicted by some mixing formula in a CMYK, RGB or CIE related color space. While this solution may not have the disadvantage of the "unstable" behavior, the resulting color may be quite far off from the reality, since mixing inks in CMYK, RGB or CIE related color spaces is known to often be inaccurate. One aspect of the present invention deals with finding a solution to this accuracy problem.

Needed is a method and apparatus that solves the aforementioned problems and combines the concepts and technology described in the Parent Patent with the technology of device profiles.

The order of printing of inks is often important. For instance if the inks would be printed in the order C-M-special ink-Y-K, we need to make sure this order is taken into account in the calculation of the overprint color, especially when the special ink has some opacity, since then it will "mask" the cyan and magenta ink, being printed underneath. The extent of the masking is dependent on the degree of opacity of the special ink. If one obtained the color of the C-M-special ink-Y-K ink combination using the device profile for obtaining the color of the CMYK inks and the colorant parameters of the special ink to obtain the color of the special ink, as if the CMYK and the special ink were not to be printed in combination, if then the color of the entire ink combination is obtained by applying some mixing formula in some color space, the opacity of the special ink would probably not be incorporated correctly and the resulting color may be quite far off from the real color.

It is another aspect of the present invention to solve the aforementioned printing order problem, which leads to inaccurate prediction of color. Needed is a more detailed description of how this problem is solved.

By accurately calculating we mean a maximum deviation between predicted color and actual color of the order of 5 CIELAB Delta E units, and an average deviation of about 2 CIELAB Delta E units.

The Prior Art for Predicting the Color of Overprints

Printing may be carried out using halftoning, also called screening, which is the process of creating the illusion of a continuous tone ("CT," "contone") image using an output (e.g., printing) device capable only of binary output (ink deposited or not deposited at any location on a substrate). For color printing, several images ("separations") are produced in the primary colorants (typically inks) used to print in color, and printed over each other in a press. For typical four color printing, four images are produced in cyan ("C"), magenta ("M"), yellow ("Y") and black ("K"), and each of these images are halftoned. Usually, digital halftoning is used together with an imagesetter, laser printer, ink jet printer, digital film recorder, or other recorder output device.

Prior to our Parent Patents (U.S. Pat. application Ser. No. 09/361,435 and U.S. Pat. No. 5,933,578), various methods were known for calculating the color resulting from superimposing a set of colorant layers on a substrate. These methods can be divided in two groups. The first group is characterized by requiring printing and measuring a relatively large number of overprints of the colorants. That is, this group includes methods that for a particular set of colorants, a particular printing technique (e.g., offset printing on a particular imagesetter), a particular substrate type (e.g., paper, or film for a photographic transparency or print, textile, sheet of plastic, etc.), a particular substrate color (e.g., the color of the paper, or of the transparent film in the case of a transparency, or of the textile, or of the plastic sheet, etc.) and a particular order of printing the colorants, involve printing a relatively large number of overprints of the colorants in the set, for example as patches. These patches are measured with a spectrophotometer or calorimeter and the measurements are used to calculate any overprint of colorants in the set using mathematical techniques, for example, interpolation. If carried out well and carefully, these methods can lead to accurate results. While these techniques can produce accurate results, and also work for halftone images, there are several drawbacks with such methods. One is that a large number of color patches of overprints need to be made. For example, the IT8.7.3 chart (American National Standards Institute [ANSI] Committee IT8 for Digital Data Exchange Standards) contains nearly a thousand patches for a four-color output. Hence it is very difficult to characterize sets of more than four colorants, for example printing with six or seven colors ("HI-FI" printing including PANTONE® Hexachrome from Pantone, Inc., Carlstadt, N.J.). There also are applications where inks other than cyan, magenta, yellow and black need to be used. Another drawback is that a set of patches will only be useful for accurately calculating overprints using the particular colorants and the particular colorant printing order used in the patches. Changing one colorant in the colorant set or changing the order of overprinting typically requires redoing the whole job of printing the set of patches.

An additional problem occurs when using such characterizations with more than four inks in a typical modem color management workflow, such as the ICC workflow. The ICC standard typically uses look up tables and interpolation to predict the CIELAB values of a particular output device. The number of nodes in these lookup tables increases exponentially with the number of inks, and the amount of computer resources becomes too high to be feasible.

Also included in this first group of known methods are those that use the well known Neugebauer equations to predict the color of an overprint of colorants, and their derivative based on Yule-Nielsen and spectral Neugebauer equations (see H. Neugebauer: "Die theoretischen Grundlagen des Mehrfarbenbuchdrucks", *Zeitschriftfur wissenschaftliche Photographie, Photophysik und Photochemie*, Band 36, Heft 4, April 1937, Arney:" Modeling the Yule-Nielsen Halftone effect," *Journal of imaging science and* technology, vol. 40, No. 3, pp. 233–238, June 1996, and Rolleston: "Accuracy of Various Types of Neugebauer Model", *IS&T and SID's Color Imaging Conference: Transforms and Transportability of Color*, pp. 32–37, 1993. These Neugebauer-like models still need the knowledge of the color of the overprints of the primary inks, so still requires measurements overprint combinations of the colorants and the gradation steps of the colorants. Also, Neugebauer equations-based methods are known not to produce accurate results.

A second group of prior art methods are those that determine spectral characterizations of individual colorants that can be used for predicting the color of overprints of so-characterized colorants. These methods, for a fixed substrate and printing technique, involve making one or more printouts of each colorant on one or more substrates, measuring the prints, and out of this data extracting a set of one or more parameters for each colorant that can be used to calculate an overprint of each colorant. These methods thus have the advantage of not requiring producing a large set of overprints. One such prior art method uses the two-parameter Kubelka-Munk method which describes an ink with one spectral parameter, $(K/S)(\lambda)$, or by two spectral parameters, scattering $S(\lambda)$ and absorption $\alpha(\lambda)$, where $\lambda$ is the wavelength. See James: "Kubelka-Munk Theory and the Prediction of Reflectance", *Rev. Prog. Coloration*, Vol. 15, pp. 66–75, 1985.

Determining the two colorant parameters involves measuring the spectrum on a bare substrate and on a black substrate, and solving the resulting equations. There also exist in the literature refinements on the two-parameter Kubelka-Munk theory that incorporate internal reflection, anisotropic scattering and other second order effects. However, these methods are applicable only for full (i.e., 100%) coverage of a layer of ink of a particular thickness, and/or are not applicable for variable ink coverages, for example, halftoning at less than 100% dot percentage. In addition, the colorant parameters they determine are neither substantially independent of the lowest substrate color nor are capable of incorporating dependencies on other ink layers. Thus these parameters are not easily applied to predicting the appearance of sequentially applied inks at less than 100% coverage wherein the substrate with the previously deposited inks may be regarded as a new substrate, with characterizable influence from layer to layer.

In summary, prior art techniques that are capable of accurately calculating overprints of inks, including rasterized (i.e., halftoned) inks, other than the techniques of the Parent Patents, require making a number of overprints of the colorants, so determining spectral parameters of a colorant that spectrally characterize the colorant. Furthermore, prior art techniques that spectrally characterize the colorants are not applicable to less than 100% coverage, do not produce parameters that are substantially independent of substrate color, and do not produce parameters that can take into account interactions between the colorant layers.

Thus there has been a need in the art for a method of characterizing colorants capable of accurately predicting the color of an overprint of the colorants without requiring measurement of overprints of the colorants and capable of predicting the color of overprints of halftones. These kinds of methods are the subject of the Parent Patents: U.S. patent application Ser. No. 09/361,435 and U.S. Pat. No. 5,933, 578. One aspect of the present invention is extending these methods for use with device profiles.

SUMMARY OF THE INVENTION

An aspect of the present invention is a method for extracting spectral properties of colorants from device profiles that do not contain any spectral data, such as ICC device profiles. A method is described for determining the colorant parameters of the colorants from such a device profile.

One embodiment is a method for predicting, e.g., calculating the color spectrum of overprints of different colorants deposited using a printing technique at a coverage percentage on a substrate of a certain substrate type. Another embodiment is an apparatus to predict the color spectrum of overprints of different colorants deposited using a printing technique at a coverage percentage on a substrate of a certain substrate type. The colorants include colorants for which there is a device profile and other colorants, such as special inks.

One method embodiment is applicable to determining an overprint of colorants that include one or more sets of colorants for which a device profile is available. The method includes indicating the printing order of the colorants and specifying the device profile for the one or more sets of colorants for which device profiles are available. One embodiment further includes transforming the sets of device profile colorants to corresponding sets of modified colorants for which each colorant has known spectral colorant parameters. One embodiment further includes modifying the colorant parameters so that the colors of the modified colorants of the corresponding device profile colorants match in color.

Briefly, in one embodiment, for each coverage percentage for which the profile has been defined, the method includes obtaining the spectra of the prints from the CIE related data in the profile. For example for offset printing, the reflection spectra are obtained.

Also disclosed is an apparatus for using device profiles and colorant parameters determined therefrom to determine the spectrum of overprints on a substrate of a set of colorants at a set of coverage percentages. The apparatus includes a first memory to store a set of one or more device profiles, each device profile corresponding to a group of colorants out of a first set of groups of colorants. The apparatus further includes a unit to determine spectral colorant parameters for each colorant in each set of device profile colorants. The apparatus further includes a converter to transform coverage percentages of the device profile colorants into coverage percentages of corresponding modified colorants, the modified colorants being spectrally defined colorants with known spectral colorant parameters that match the device profile colorants. In one embodiment, the color gamut of the modified colorants is broader than that of the device profile colorants.

In one embodiment, the apparatus further includes a second memory for storing the spectrum of a substrate that matched the substrate of the reproduction process, and a unit that uses spectral colorant parameters to determine the color of set of colorants being printed on top of each other at different coverage percentages.

Also disclosed is a method and apparatus for simulating the appearance of overprints of a set of colorants on a display using both device profiles and colorant parameters.

These and other objects, features, aspects and advantages of the present invention will become more apparent from the following detailed description of preferred embodiments with the accompanying drawings.

DETAILED DESCRIPTION OF THE PREFERRED EMBODIMENTS

Figure 3:
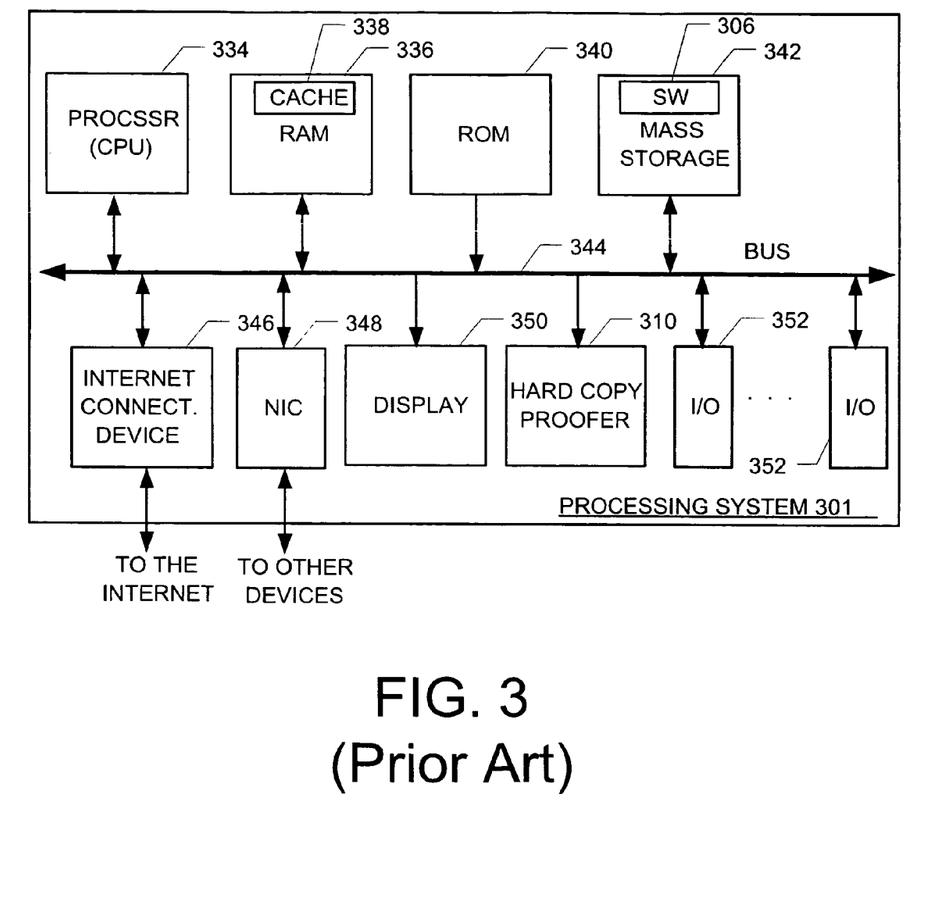
FIG. 3 is a simplified block diagram of a processing (computer) system 301 in which the present invention may be embodied.

FIG. 3 is a simplified block diagram of a computer system 301 in which the present invention may be embodied. Embodiments of the present invention may be embodied in a general-purpose computer system such as shown in FIG. 3, and the remaining description will generally assume that environment. However, the invention may be embodied in dedicated devices such as printer servers and printer controllers. A computer system configuration such as that of FIG. 3 is standard, and as such, FIG. 3 is labeled "Prior Art." A computer system such as system 301, suitably programmed to embody the present invention, however, is not prior art.

In accordance with known practice, the computer system includes one or more processors 334 that communicate(s) with a number of peripheral devices via a bus subsystem 344. These peripheral devices typically include a memory subsystem 336 shown comprising RAM and a cache 338, a user input facility (one of input devices 352), a display subsystem 350, output devices such as a printer 310, and a file storage (mass storage) system 342.

In this context, the term "bus subsystem" is used generically so as to include any mechanism for letting the various components of the system communicate with each other as intended. With the exception of the input devices and the display, the other components need not be at the same physical location. Thus, for example, portions of the file storage system could be connected via various local-area or wide-area network media, including telephone lines. Similarly, the input devices and display need not be at the same location as the processor, although it is anticipated that the present invention will most often be implemented in the context of personal computers (PCs) and workstations.

Memory subsystem 336 includes a number of memories including a main random access memory ("RAM"). It may also include read only memory ("ROM") in which fixed instructions are stored. In the case of Macintosh-compatible personal computers this would include portions of the operating system; in the case of IBM-compatible personal computers, this would include the BIOS.

I/O devices 352 may include a keyboard and may further include a pointing device and a scanner. The pointing device may be an indirect pointing device such as a mouse, trackball, touchpad, or graphics tablet, or a direct pointing device such as a touchscreen incorporated into the display.

Display subsystem 350 typically includes a display controller and a display device coupled to the controller. The display device may be a cathode ray tube ("CRT"), a flat-panel device such as a liquid crystal display ("LCD"), or a projection device. Display controller provides control signals to display device and normally includes a display memory (not shown in the figure) for storing the pixels that appear on the display device.

The file storage system provides persistent (non-volatile) storage for program files 342 and data files, and typically includes at least one hard disk drive. There may also be other devices such as a floppy disk drive, a CD-ROM drive and optical drives. Additionally, the system may include hard drives of the type with removable media cartridges. As noted above, one or more of the drives may be located at a remote location, such as in a server on a local area network or at a site on the Internet's World Wide Web.

The Determination of Spectral Parameters from a Device Profile

By way of illustration, a method for determining spectral parameters from an output device profile is described. Such an output profile describes the colorimetric behavior of an output device, such as a printer, imagesetter and printing press, or other color reproduction output device.

Two cases are distinguished. In the first case, the device profile includes no spectral information, as is the case with common ICC profiles. In the second case, the device profile includes the spectral characteristics of the device, as might be the case, for example, for some proprietary profiles. Method embodiments are described herein for determining the spectral colorant parameters from both device profiles that include spectral information and those that do not include such spectral information.

Profiles Containing Spectral Information

A typical profile such as an ICC profile contains a table of device independent color values, e.g., CIE Lab values and the overprint that produced them, including, for example, different coverage percentages of one ink, two inks, etc.

It may be that a profile that contains spectral information is available. One embodiment is applicable to a device profile that includes the spectrum, e.g., the reflectance spectrum for different overprints of the inks when printed in a printing order. One method of determining the spectrum parameters in such a case uses results of the first Parent Patent (U.S. Pat. No. 5,933,578), which described how to determine a set of parameters such as the three parameters $\alpha_i(p_i, \lambda)$, $\mu_i(p_i, \lambda)$, $S_i(p_i, \lambda)$ that can characterize the calorimetric properties of an ink layer as it pertains to overprints of several such layers. Here, $p_i$ is the amount of ink—e.g., the ink coverage—in the $i^{th}$ ink layer, with the amount expressed as a fraction between 0 and 1, and λ is the wavelength of the light radiation. Using such parameters, when there is no interaction between the layers, the reflectance spectrum $R_i(\lambda)$ of the $i^{th}$ ink layer can be determined by applying the following equation recursively:

$$R_i(\lambda)=(1-\alpha_i(p_i,\lambda)*R_{i-1}(p_i,\lambda)^{\mu_i(p_i,\lambda)}+S_i(p_i,\lambda), \quad (1)$$

with $R_0(\lambda)$ being the spectrum of the bare substrate.

Figure 4:
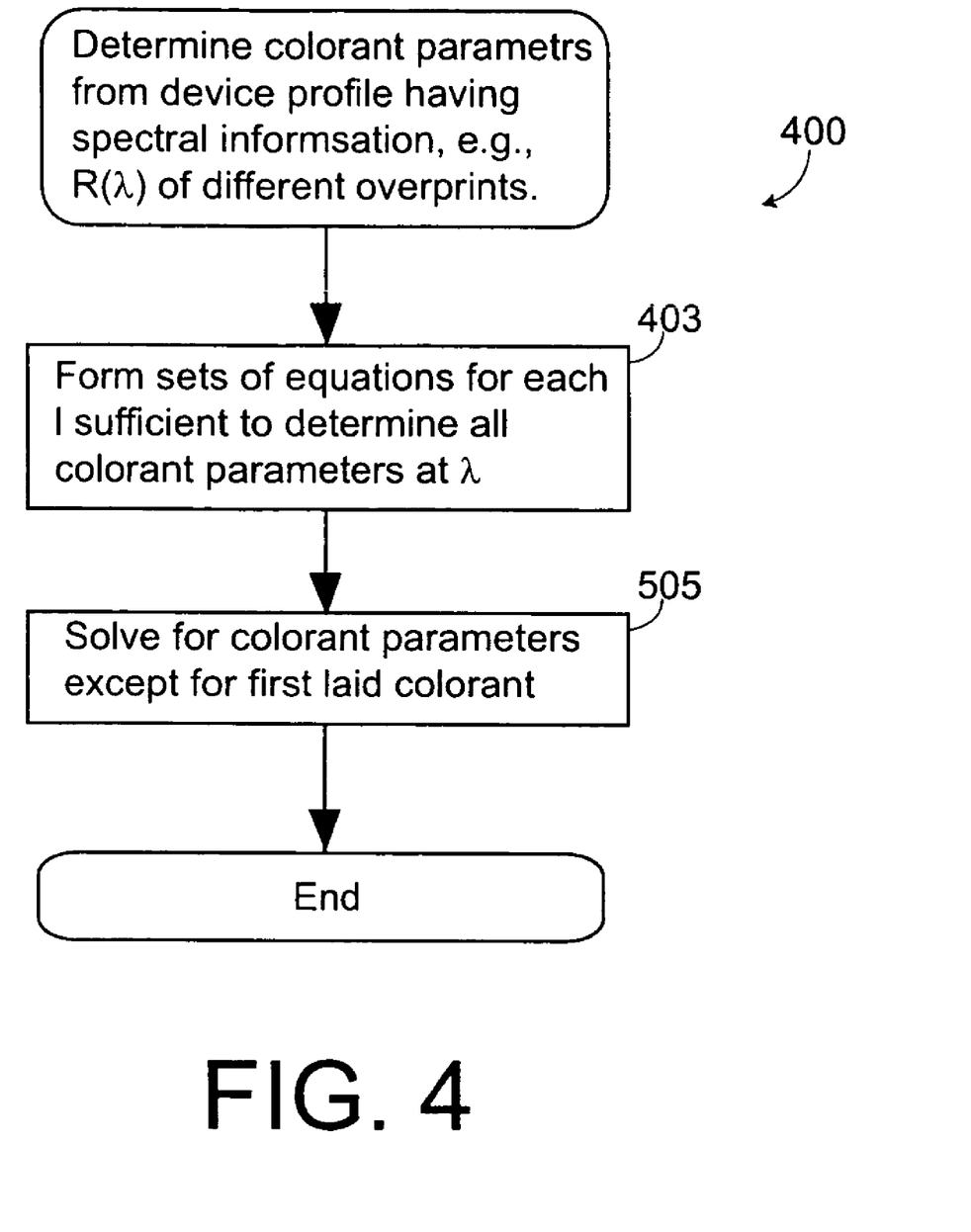
FIG. 4 shows a flowchart of an embodiment of a method to determine the colorant parameters from device profiles having spectral information.

The device profile containing the spectral information includes the reflectance spectrum for value values of λ for various overprints of the CMYK for the color reproduction process on the particular substrate of the profile. Thus, for a set of wavelengths, the left hand side of Eq. 1 is known for several values of $p_i$ for various overprints. At each wavelength, there are three unknowns per colorant, so altogether 12 unknowns. FIG. 4 shows one method embodiment 400 of determining the colorant parameters of a set of colorants that are in a device profile that includes spectral information. In a step 403, the spectral information in the device profile is used with Eq. 1 and the information on percentage coverage of each overprint in the device profile so set a sufficient number of equations with the three colorant parameters of the four colorants as unknowns. In a step 405, the questions are solved, preferably numerically, to determine the colorant parameters of each of the overprinting colorants of the profile. The colorant parameters of the first-printed colorant may not be determined because the spectrum of the bare substrate, $R_0(\lambda)$ is typically not available; only $R_1(\lambda)$, $R_0(\lambda)$, $R_3(\lambda)$, and $R_4(\lambda)$ are available for the four-colorant case. However, if this colorant is always going to be printed first and if there is no interaction between the different colorants, then there is no need to have the spectral colorant parameters of this colorant—only $R_1(\lambda)$ for different values of $p_1$.

Profiles Containing no Spectral Information

Figure 5:
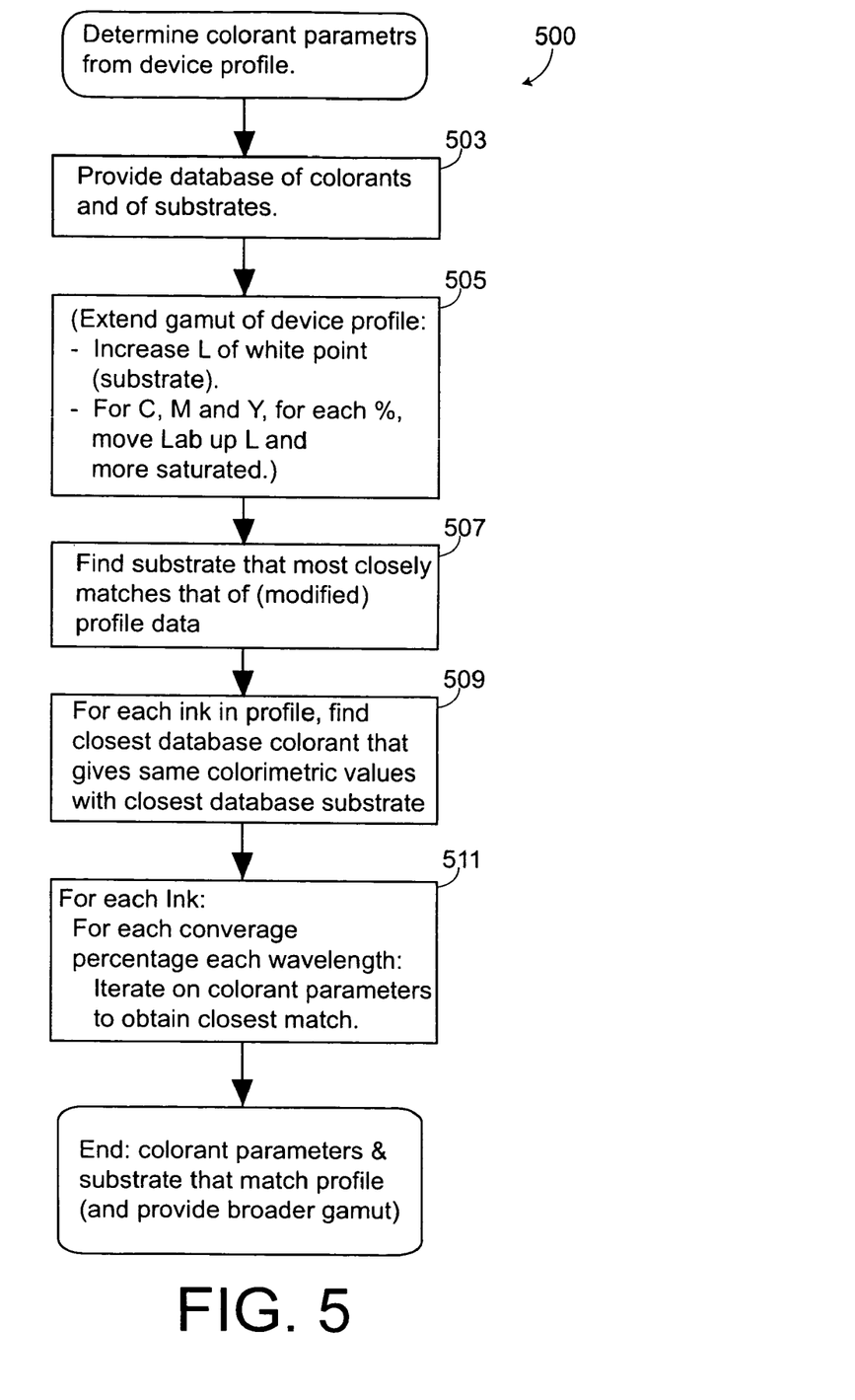
FIG. 5 shows a flowchart of an embodiment of a method to determine the colorant parameters from device profiles that has no spectral information.

FIG. 5 shows a second method embodiment 500. In a step 503, a database is provided of information about different substrates—e.g., paper stocks—and about different colorants, printed at different coverage percentages. In one version, the information is in the form of reflection spectra. In a second version, the colorant information is in the form of colorant parameters. The data in the database is searched for a match with the data in the device profile. When the calorimetric data from the device profile can be matched with colorimetric information determined from the data in the database, it is assumed the needed colorants and substrate are found in the database.

The case is discussed of the data stored in the database being in the form of colorant parameters for the colorants, and spectra of the substrates. In a step 507, a substrate search is first carried out. The colorimetric values, e.g., CIE Lab of the substrate is available in the profile; these are the 0% coverage values. For each substrate in the database, the CIE Lab values are determined from the database data, and the closeness to the profile substrate color is determined, in ΔE values in one embodiment. The best match substrate is the one that produces the lowest $\Delta E^2$.

In a step 509, the closest colorants for the selected closest substrate are found. Each colorant, C, M, Y, and K, is considered at 100%. The calorimetric value of 100% of a single colorant from the profile is compared to each of variants of the same colorant in the database, e.g., all the different cyans in the database, etc., by calculating the spectrum using Eq. 1 with the selected substrate and then determining the color in CIE Lab and then determining the ΔE value. The spectrum to color conversion is carried out using any standard method to determine colorimetric values from spectra in the color independent space used for the device profile, e.g., CIE Lab or CIE XYZ. Thus the C, M, Y, and K colorants in the database that most closely match the profile colorants are obtained.

Step 509 may provide a perfect match or a close enough match between the colors in the profile and the colors that would occur from colorants in the database. In such a case, in a step 511, the colorant parameters of the closest database colorant parameters are modified to obtain a perfect color match. Each colorant parameter is a function of coverage percentage and wavelength. At each coverage percentage of the device profile and at each wavelength of the parameters in the colorant database, the colorant parameter values that provide the closest color match (minimum $\Delta E^2$) are determined by an iterative method starting with the closest database match values of the parameters as obtained in step 507. The result of step 509 is a set of colorants that correspond to the colorants of the profile, match colors with the colorants of the profile, have a wider gamut than the colorants of the profile, and have colorant parameters that are known. Associated with the colorants is a substrate that matches the device profile substrate and that has a known reflectance spectrum. We call such colorants "modified" colorants herein, and we call colorant parameters of the modified colorants and the spectrum of the associated substrate the "modified colorant data" herein.

In an alternate method embodiment, the color values of the device profile colorants are first modified to cover a wider color gamut than the device profile itself. This is shown as step 505 in FIG. 5. First, the white point of the device profile us made "whiter" by increasing the L value. The search for the associated substrate thus produces a substrate that closely matches the device profile substrate but with a wider gamut, and that has a known reflectance spectrum. Then, for each non-black colorant, at each coverage percentage in the profile of the colorant alone, the CIE Lab value is modified by moving the L value up towards the new white point, and increasing the a and b values radially to provide higher saturation. The amounts by which the L value and the a and b values are modified are in proportion to the colorant coverage percentage. For the black colorant, the L value is reduced to provide a "blacker" black. Thus, the CIE Lab values of the substrate and of each of the colorants individually on the bare substrate are modified such that a substrate and colorants matched to these CIE Lab values provide a wider gamut. Therefore, the closest substrate matched in step 507 and the closest colorants matched in steps 509 and 511 produce a wider gamut than the colorants of the device profile. Thus, The modified colorants have modified colorant data that produces a wider spectrum.

In an improved embodiment, dot gain mismatch also is considered. The device profile may have been established for a certain printing technique that has a different dot gain than the printing technique used to determine the colorant parameters of the colorants in the colorant database. In the improved embodiment, a mapping is first made between the coverage percentages in the profile and the coverage percentages of the data in the database. In one version, a determination is made of what coverage percentage in the database corresponds to each coverage percentage in the device profile. In a second version, described below, the dot gain is accounted for in a mapping from a color of an overprint of the colorants in the database to an overprint of modified colorants, i.e., colorants that color match and have a wider gamut than the profile colorants, and whose colorant parameters are known.

One embodiment of first version includes for each percentage of the colorant in the profile, determining the CIE Lab value from the profile, extending the CIE Lab value to broaden the gamut, then, for each case of the same colorant in the database, i.e., each of the cyans, each of the magentas, etc., determine the CIE value and for each of the database coverage percentages and search for what percentage provides the closest color match. The result for each of the cyans in the database is a mapping of what coverage percentages are closest to the profile provided coverage percentages.

The result of including both the dot gain compensation and color matching provides the associated substrate spectrum, and for each coverage percentage in the profile for each colorant in the profile, the colorant parameters of set modified colorants, and a mapping of coverage percentages of each the profile colorants to percentage of each corresponding modified colorant.

Determining a Mapping of Profile Colorants to Modified Colorants

Figure 6:
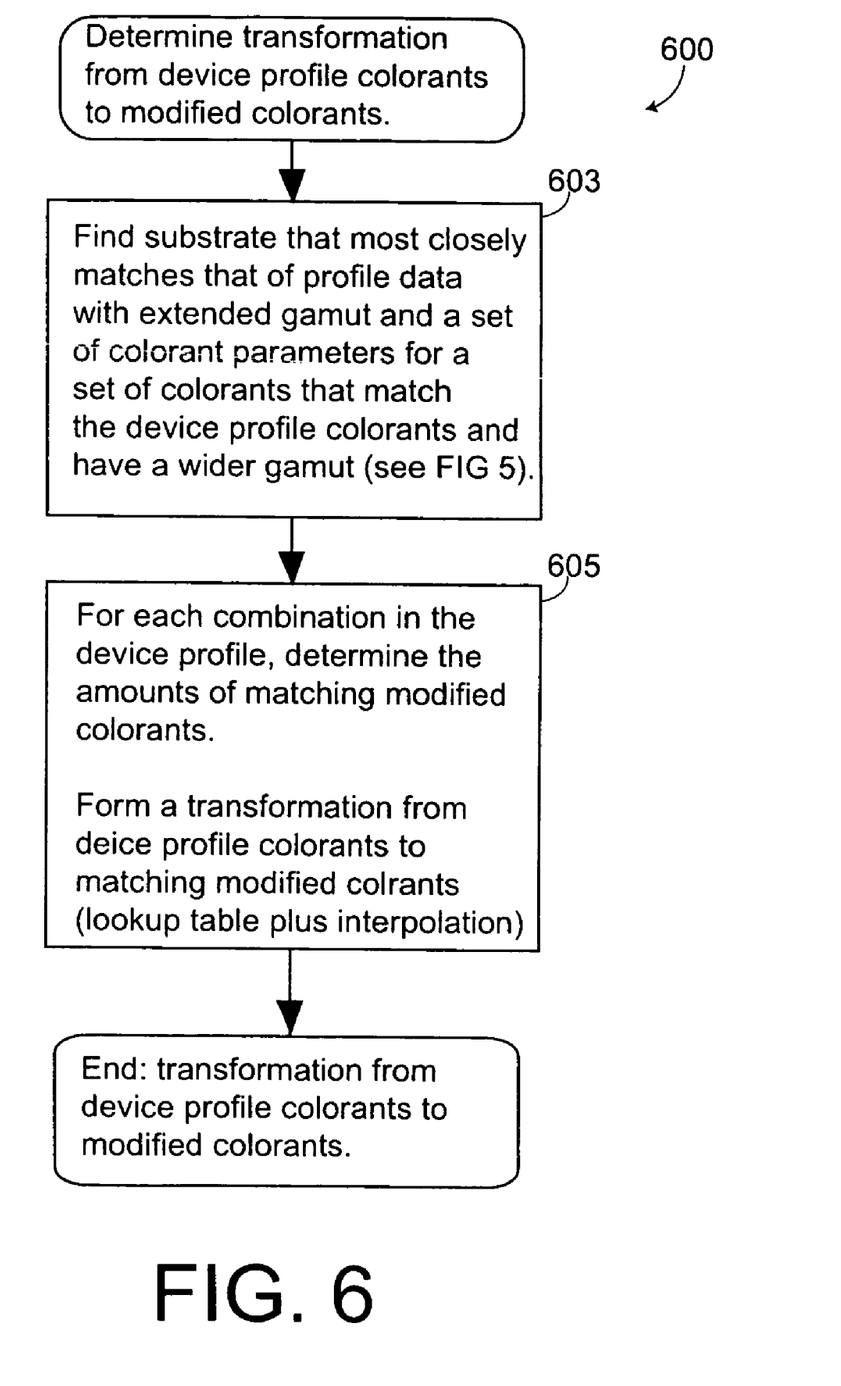
FIG. 6 shows a flowchart of an embodiment of a method to determine a transformation from device profile colorants to modified colorants that provide a color match with the device profile colorants, for which colorant parameters are known, and that in one embodiment provide a wider gamut.

FIG. 6 illustrates in flowchart form a method 600 of determining a color mapping that can map an overprint of amounts of standard CMYK colorants as provided in a device profile to amounts of modified colorants such that the color of the overprint of the modified colorants matches the color of the overprint of the profile colorants. The modified colorants are as described above, i.e., they each have known colorant parameters on a selected associated substrate that matches the profile substrate but with a wider gamut and that has a known spectrum, and they provide a color match of an overprint of the profile colorants, but a wider spectrum.

In a first step 603, the modified colorants and their colorant parameters that match the device profile colorants are determined. This follows the process 500 described above. In a next step 605, using these modified colorants, a transformation is built for determining an overprint of the modified colorants from any overprint of the device profile colorants such that the colors match. That is, a mapping that converts any set of coverage percentages of the device profile colorants, e.g., CMYK to a set of coverage percentages of the modified colorants, denoted C'M'Y'K' in the CMYK case, such the C'M'Y'K' matches the color of the CMYK overprint. One embodiment is as described in U.S. Pat. No. 5,689,349 to Plettinck, et al. titled METHOD AND DEVICE FOR GENERATING PRINTING DATA IN A COLOR SPACE DEFINED FOR NON-STATNDARD PRINTING INKS, hereby incorporated herein by reference. U.S. Pat. No. 5,689,349 describes a method to transform a first color coordinate set—CMYK in our application—to a second colorant set—C'M'Y'K' in our application—preserving color appearance. The method includes determining the color specified with the CMYK colorant in a first device independent color space. This color is transformed to a second device independent color space for gamut mapping. Because in our application, the C'M'Y'K' colorant space has been determined in such a way that the color gamut is slightly larger than the color gamut of the CMYK colorants, in one embodiment the first and second device independent color spaces are identical, so that no transforming to a second device independent color space takes place. The method next estimates the coverage percentages of the C'M'Y'K' colorants that produce the color in the second device independent color space. This estimation is subsequently refined until the method obtains the coverage percentages C'M'Y'K' that produce the color in the second colorant space exactly.

In one embodiment, each CMYK combination in the device profile is transformed to a matching C'M'Y'K' amount. This forms a lookup table. The transformation can then be built by a combination of a table and multi-dimensional interpolation. How to build such a transformation is known in the art. One embodiment uses a method as described in U.S. Pat. No. 5,268,754 to Van de Capelle, et al., titled METHOD AND DEVICE FOR CONVERTING A COLOR COORDINATE SET, hereby incorporated herein by reference. In particular, the transformation from a CMYK combination to a matching C'M'Y'K' combination includes a tetrahedral interpolator.

Determining the Color of an Overprint of a Combination of Standard and Additional Colorants One embodiment of a method to predict the color of an overprint of a set of colorants at a set of respective coverage percentages on a substrate of a substrate type using a printing technique includes providing one or more device profiles for one or more subsets of the set of colorants for printing on the substrate with the printing technique and determining the colorant parameters of the device profile colorants of the subsets. The colorant parameter determining may be as described above. The method further includes providing the colorant parameters of the non-device profile colorants. The method further includes determining the spectrum of the substrate. The color spectrum of the overprint is now determined, using, for example Eq. 1.

Figure 1:
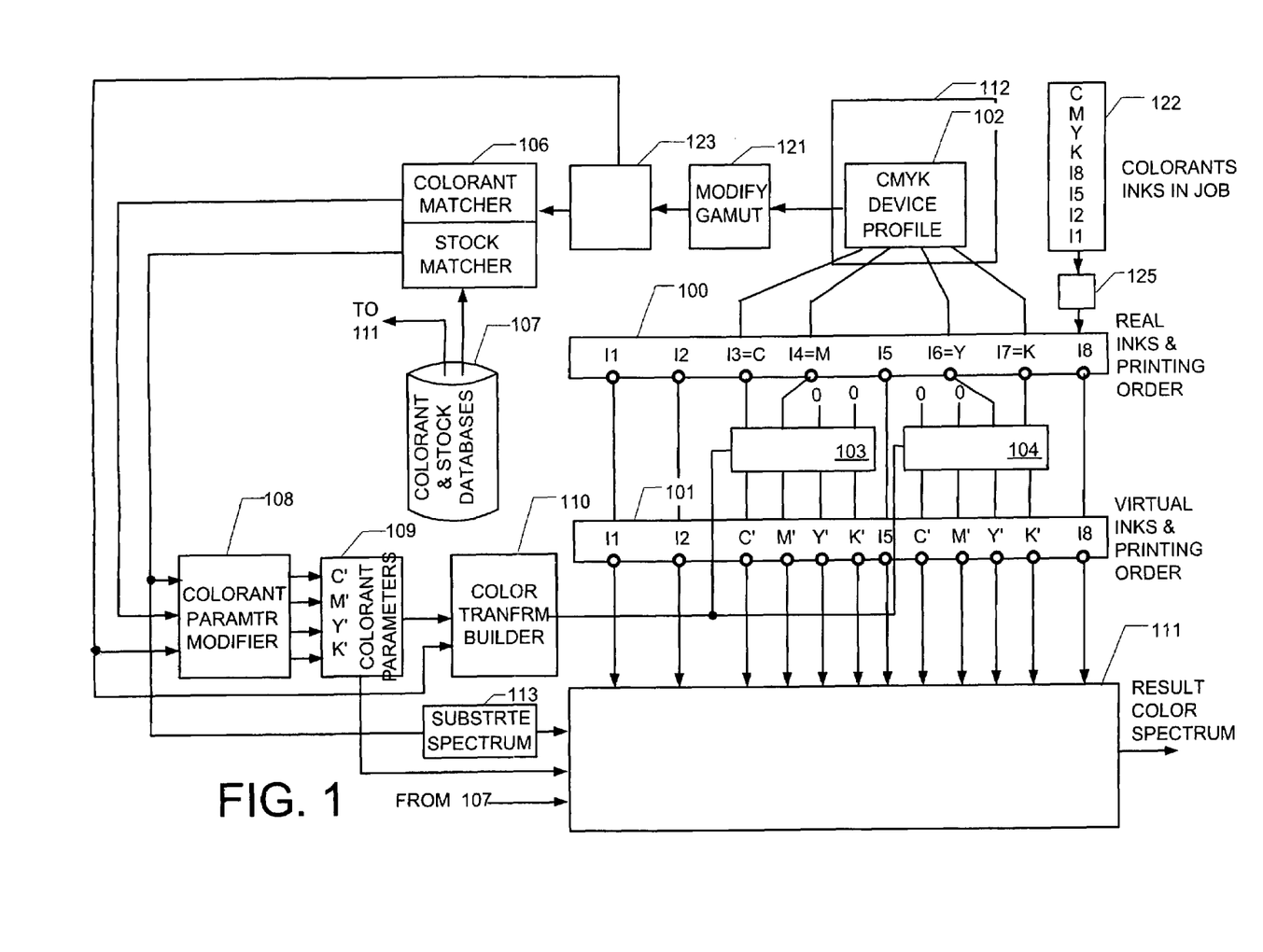
FIG. 1 Gives an overview of one embodiment of the invention, and shows the different elements used to solve the problem of combining device profiles and ink profiles and overcoming the aforementioned problems. Some of the elements in this drawing are described in the Parent Patents incorporated herein by reference.

FIG. 1 illustrates block diagram for determining the color, e.g., the spectrum of a overprint of standard colorants for which a device profile is provided, and additional colorants using the output device of the provided profile. The block diagram shown provides for describing a method embodiment that includes a set of steps, and also provides for describing an apparatus embodiment. Suppose there is a set 122 of colorants used in a job. In this case, there are 8 colorants, denoted I1, I2, . . . , I8, with Ii indicating the i'th colorant, i=1, . . . , 8. Thus, I1 is the first colorant printed, and I8 the eighth. In this example, four of the inks are standard CMYK as provided in a device profile 102 stored in a first memory 112. Thus, the device profile colorants are CMYK. The device profile is matched to the substrate and the printing process. The device profile colorants are printed as follows: the third printed ink, I3 is C, the fourth, I4 is M, the sixth, I6 is Y, and the seventh, I7 is K. The first step of the method sorts the colorants (process 125) according to their printing order to obtain a sorted set of colorants 100.

A database 107 of colorants and substrates is provided in the form of the spectra of the substrates and the colorant parameters of the colorants, including the non device profile colorants I1, I2, I5, and I8. In a gamut modifying process 121, the gamut of the device profile colorants and of the device profile white point is extended as described above. This produces a set 123 of color values for each of the coverage percentages of each colorant in the profile 102. A matching process 106 determines a best matching colorant for each device profile colorant and having a wider gamut than the profile colorants. The matching process 206 further searches the database for the best matching substrate, again that produces a wider gamut. The matching process 106 operates as described above. In one embodiment, the colorant parameters of the best database match are modified to produce an even better color match to the device profile colorants. This is accomplished by the colorant parameter modifier 108. The result is a set of modified colorants with the colorant parameters 109 stored in memory, and a substrate spectrum 113 stored in memory.

In one embodiment of the invention, this best matching substrate is the best match substrate from the database. In another embodiment, the best database substrate spectrum is modified to produce an even better match with the device profile substrate by an iterative method similar to modifying the colorant parameters of the best match database colorants.

Color transform builder 110 builds a transformation from the color space of the device profile colorants to the modified colorants. One embodiment of the color transform builder 110 uses the method of U.S. Pat. No. 5,689,349 to Plettinck, et al., as described above. The result is a transformation based on table lookup and multidimensional interpolation for transforming CMYK coverage percentages into the C'M'Y'K' modified colorant coverage percentages.

Because the printing order of the CMYK is C, M, then I5, and then Y and K, the C and M, and the Y and K are separately converted into respective sets of C'M'Y'K'. Thus, the color transformation determined by 110 are stored into two color converters 103 and 104, respectively, each able to transform CMYK coverage percentages into the C'M'Y'K' coverage percentages. Converter 103 converts the C and M, and converter 104 converts the Y and K, respectively, are used in the embodiment shown in FIG. 1. Colorant set 101 is the coverage percentages of the modifier inks and other inks. We call these the virtual inks, because if they existed, the overprint of their respective coverage percentages would match the real colorant set 100. The set of virtual colorants is used here to calculate the color. As a consequence of separately converting CM and YK, the number of "virtual" colorants is increased to be four more than the number of real colorants in set 100. In other cases, there may be more or fewer virtual colorants depending on the number of intervening non-CMYK colorants in the printing.

The resulting coverage percentages of the set of colorants 101, each colorant are fed into a device 111 (or process in a method embodiment) that calculates the resulting color. The colorant parameters of the modified colorants obtained from 109, those of the non-device profile colorants from database 107, and the substrate spectrum 123 are provided to device 111 for the calculation. In one embodiment, the calculation uses Eq. 1 (described in the Parent Patent U.S. Pat. No. 5,933,578).

Figure 2:
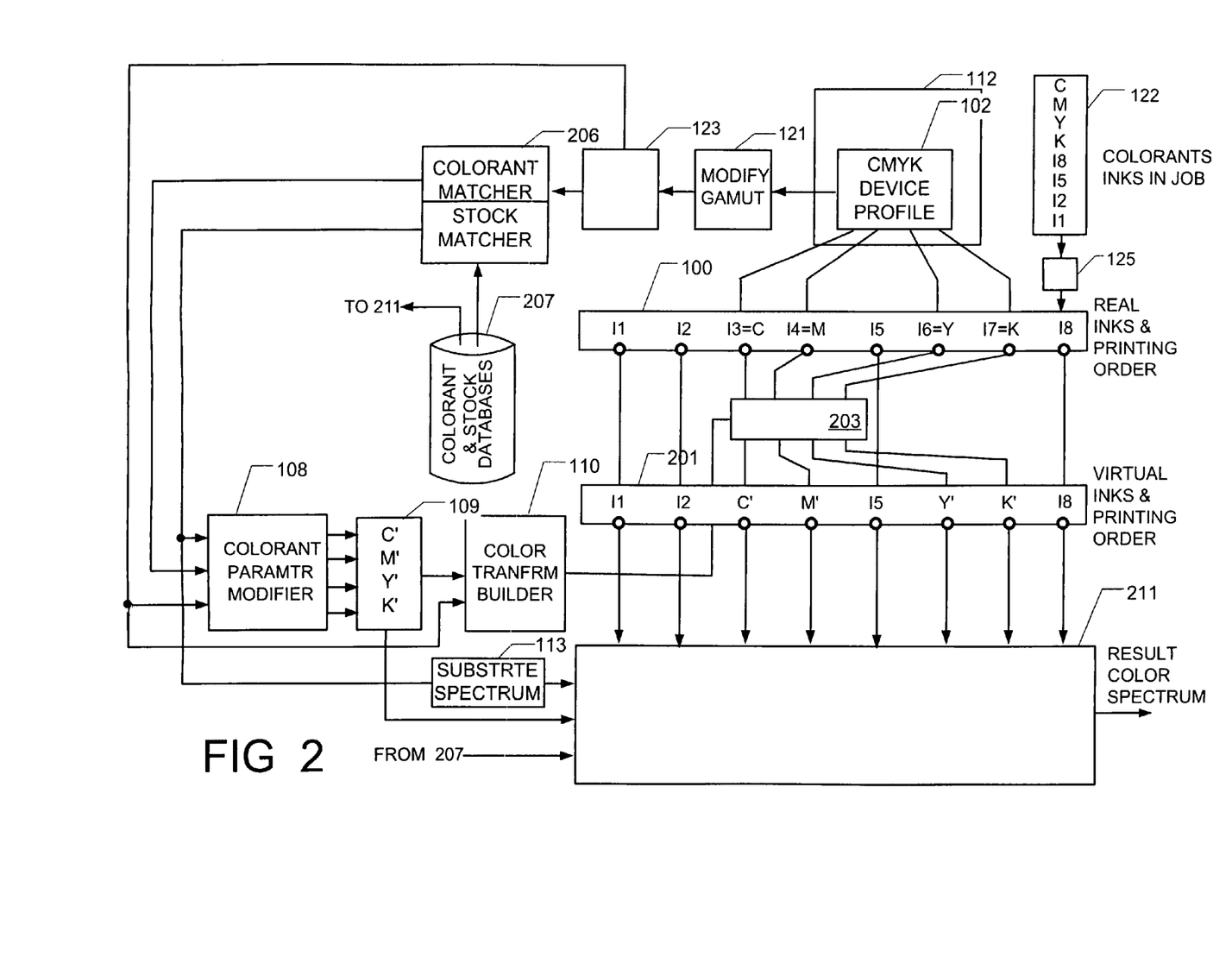
FIG. 2 Gives an overview of another embodiment of the present invention, differing from the embodiment shown in FIG. 1, in the aspect of keeping the same number of inks being fed to the logic unit calculating the color of the overprint of all colorants, as there have been inks specified in the job.

An alternate configuration is shown in FIG. 2 that can be used to form an alternate method embodiment or an alternate apparatus embodiment. In FIG. 2, a single color converter 203 is used to obtain the C'M'Y'K' colorants and then the virtual ink set (now shown as 201) orders I5 between the C'M' and the Y'K' modified colorants. While this does not increase the number of colorant coverage percentages input into the color calculation device (now shows as 211), the resulting color spectrum may match the overprint color slightly less accurately.

Method and Apparatus of Simulating Prints on a Proof Printer or on a Display

It would be clear to one with ordinary skill in the art, and from the incorporated by reference Parent Patents, that an apparatus built from the above description and FIG. 1 or FIG. 2 can also be used in an apparatus to display images on a display, such as a CRT monitor, or to print an image on a printer.

Another aspect of the present invention is an apparatus for determining the spectrum of colorant overprints. This is applicable to both transmittance and reflection imaging, and only the reflection case will be described. How to extend to the case of transmission imaging would be clear to those of ordinary skill in the art.

Figure 7:
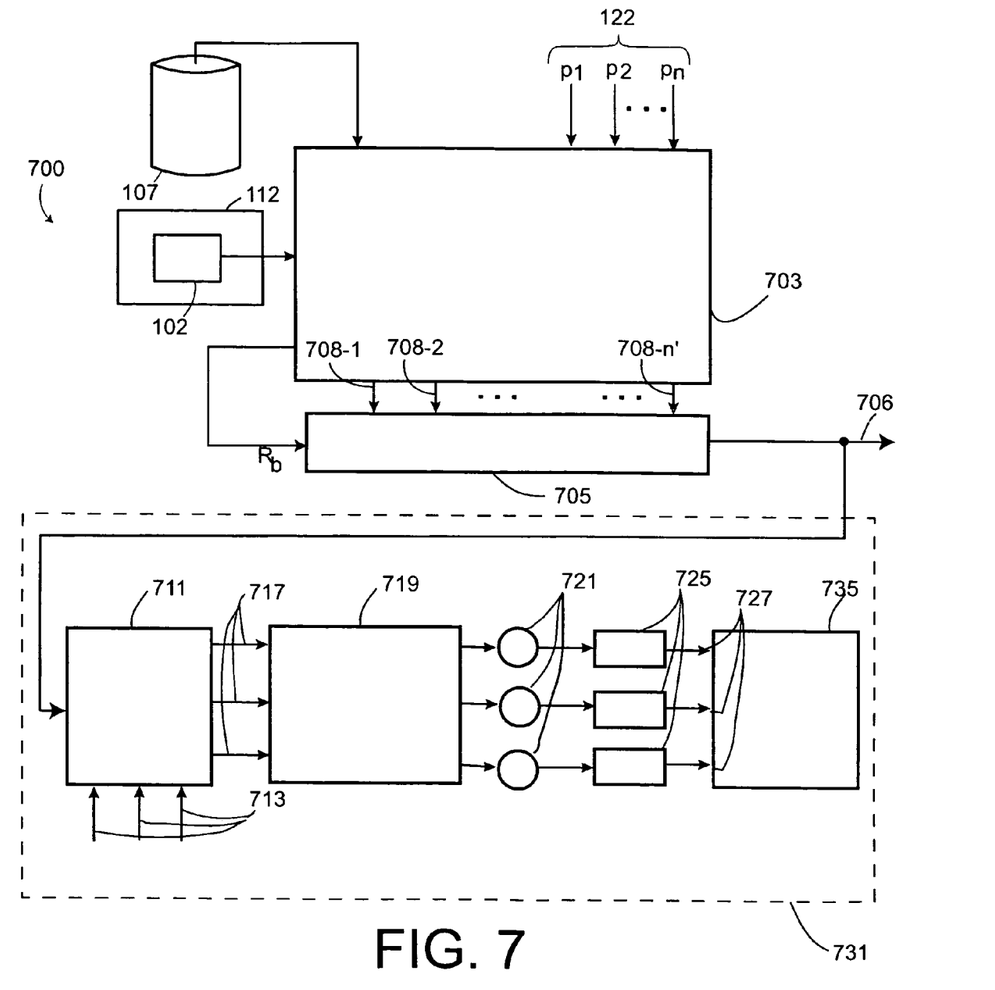
FIG. 7 shows an apparatus for determining the spectral color parameters of colorants and for determining the color spectrum of overprints according to an embodiment of the invention. Included in this diagram is an apparatus for using the color spectrum of overprints to simulate color appearance on a CRT display.

The preferred embodiment of the apparatus of the present invention is shown as item 700 in FIG. 7. Apparatus 701 calculates the color spectrum of an overprint of n colorants with respective coverage percentages $p_1, \ldots, p_n$ on a background with background reflectance $R_b(\lambda)$. Some of the n colorants are those of a device profile 102 shown stored in a memory 112. It is assumed that each of the other colorants has been characterized, for example using one of the embodiments of the Parent Patents. That is, each non-device profile colorant has been characterized by either two spectral parameters (no layer interaction, no scattering), three spectral parameters (no layer interaction, scattering), or more than three spectral parameters (layer interaction). That is, each non-device profile colorant has a set of $n_p$ colorant parameters. The parameters of the non-device profile colorants and of other colorants are provided in a database 107 that also includes the reflection spectra of some known substrates. In one embodiment, each of the colorant parameters and spectra are quantized into a finite number, denoted $n_l$, 36 in one embodiment, of wavelengths $\lambda_1, \lambda_2, \ldots, \lambda_n$.

Apparatus 700 has access to the database 107 and has as input n signals representing the n colorant coverage amounts (dot percentages of inks for the case of offset printing) denoted $p_1, \ldots, p_n$, respectively. Apparatus 700 further includes a logic unit 703 coupled to the n inputs, to the device profile memory 112 and to the database 107. Logic unit 703 determines the closest substrate spectrum $R_b(\lambda)$ as described above. Logic unit 703 further determines a set of modified colorants that match the device profile colorants, but that has a wider spectrum. The logic unit 703 further determines the colorant parameters of the modified colorants, either by selecting the closest colorants from the database or by modifying colorant parameters from the database, as described above. The logic unit 703 further includes one or more color converters that convert the coverage percentages of the device profile colorants to coverage percentages of the modified colorants. The logic unit 703 further is to determine a set of "virtual" inks comprising one or more instances of modified inks and the non-profile inks in a printing order, and for each such virtual ink, the coverage percentage for producing a match. Denote by n' the number of such virtual inks. The logic unit 703 determines n' coverage denoted $p'_1, \ldots, p'_{n'}$ percentages. The logic unit also determines and outputs n' sets of colorant parameters, denoted 708-1, 708-2, ..., 708-n', respectively of each of the virtual inks at each of the n' coverage percentages. The colorant parameter sets at the n' converage percentages are input to a combiner unit 111 that determines the spectrum 706 of the combination. The logic unit 703 provides to the combiner 111 the substrate spectrum $R_b(\lambda)$. The values of the colorant parameters for the non-profile colorants are obtained from databse 107, and values of the colorant parameters of the modified colorants are determined as described above. The output 706 of the combiner unit 705 is the color spectrum at the $n_l$ wavelengths resulting from overprinting the n colorants at coverage percentage $p_1, \ldots, p_n$, respectively, when deposited over the substrate.

Figure 8:
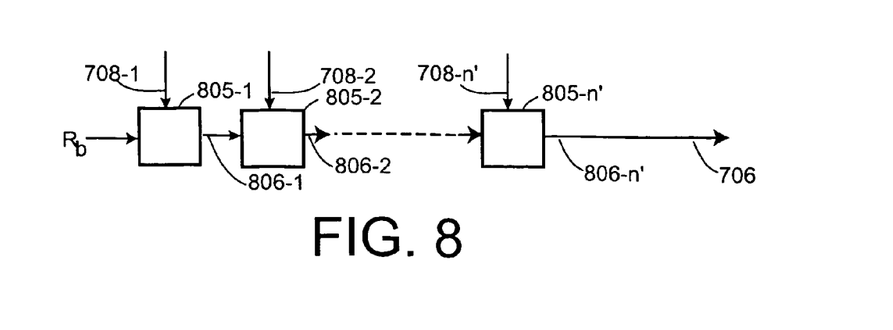
FIG. 8 shows an apparatus that is one embodiment of part of the apparatus of FIG. 7.

One embodiment of combiner unit 705 is shown in FIG. 8. The 708-1, 708-2, ..., 708-n' of logic unit 703, are n' sets of spectral colorant parameters of the n modified and non-device profile colorants at $p=p'_1, \ldots, p'_{n'}$, respectively. These outputs are coupled to n' arithmetic units 805-1, 805-2, ..., 805-n', each arithmetic unit also having a second input. The second input of the first arithmetic unit 805-1 is coupled to the background spectrum input $R_b(\lambda)$. The second input of each subsequent arithmetic unit is coupled to the output of the previous arithmetic unit. The output of each arithmetic unit 805-i, i=1, . . . , n', is the color spectrum of the colorant of coverage percentage $p_i$ when deposited over the substrate only (for i=1) or when deposited over the substrate with all the colorants 1, . . . , i–1 deposited in order, for other values if i. Each arithmetic unit 805-i, i=1, . . . , n', uses for instance Eq. (1). In one embodiment, each arithmetic unit 805-i, i=1, . . . , n', includes: (a) an exponentiation unit which, for each wavelength, exponentiates the value of the signal of the second input by the first colorant parameter from the first input, that is, determines (the second input)\*\*(the first colorant parameter of the first input), where \*\* is exponentiation; (b) a multiplication unit which multiplies the result of the exponentiation by the value of the second colorant parameter from the first input; and (c) an adder unit which adds for each wavelength the value of the third colorant parameter (if any) from the first input to the result of the multiplication and exponentiation. Thus, arithmetic unit 805-1 calculates the reflectance spectrum of the print of colorant 1 at coverage percentage $p'_1$ on the substrate with spectrum $R_b$ resulting in a spectral color $R_{b+Color\ 1}(\lambda)$ In arithmetic unit 805-2, the effect of colorant 2 at coverage percentage $p_2$ is added by using the same method as arithmetic unit 805-1, but now $R_{b+Color\ 1}(\lambda)$ takes the place of the background color. The final output 806-n is the reflection spectrum 706 of the superimposition of all the colorant layers.

Not shown in apparatus 700 of FIG. 7 and 800 of FIG. 8 are the control units necessary to operate the various blocks. Including such control units would be clear to those of ordinary skill in the art. Each of the blocks in apparatus 700 of FIG. 7 and 800 of FIG. 8 may be implemented in various ways. For example, each may be implemented as a set of computer instructions operating on a computer system. Alternatively, some or all blocks may be built using special hardware, for example using digital signal processor ("DSP") devices, or using programmable logic, or using special purpose logic, for example, one or more application specific integrated circuits ("ASICs"). It would be clear to those in the art that many ways of implementing the apparatus is possible, and how to design such specific implementations would be clear to those of ordinary skill in the art.

In practice, the method is used to predict the color of an image comprising of pixels, and thus, includes predicting many overprints, each corresponding to a pixel in the image.

Method and Apparatus of Simulating Prints on a Proof Printer or on a Display

Referring again to FIG. 7, another aspect of the invention is a method and apparatus for determining color values, for example CIE XYZ values or CIE-Lab or other color values of an overprint of n colorants on a substrate using the colorant parameters determined according to the above aspects of the invention. Yet another aspect is using these color values for simulating the visual appearance of an overprint of n colorants on a substrate on a display, for example, CRT monitor 735 of a display subsystem a computer system, or on a printer, for example, a proof printer. The emphasis of the description herein is on an apparatus for such determination, and it would be clear to those of ordinary skill in the art from this description how to implement the conversions and simulations as a method.

In practice, the color values are those of an image comprising of pixels, and thus, determining the color values of an overprint is repeated for many overprints, each corresponding to a pixel in the image.

Additional apparatus for these aspects of the invention is shown as apparatus 731 in FIG. 7. One may apply one or more of the embodiments of the method and apparatus of the present invention to determining color values, for example CIE XYZ values of an overprint of n colorants on a substrate. Similarly, CIE-Lab or other values may alternatively be determined. In another aspect of the present invention, these CIE-XYZ values can then be converted to RGB values to produce RGB signals to drive a color monitor, for example, CRT monitor 735. The image on the CRT is then used as an accurate simulation of the overprint of the n colorants. In FIG. 7, controller and CRT display 731 includes the hardware apparatus for displaying the overprint, and takes as input the reflection spectrum 706 which is the output of apparatus 701. As stated above, these blocks also may be implemented as a set of method steps implemented on a computer. The spectrum from apparatus 700 or another alternate apparatus is fed into a color values converter, shown as 711. In the preferred embodiment of the apparatus, $3*n_l$ multiplier adders are used, which have as additional input the CIE illuminant-observer weightings 713. The output 717 is the set of CIE-XYZ values. How to carry out this conversion operation from a spectrum to CIE values is known in the art. The CIE-XYZ values 717 are fed into color coordinate converter, which preferably includes a 3×3 matrix multiplier 719, three adders 721, and three lookup tables 725 with the adder outputs as inputs, the lookup tables for gamma correction to produce the RGB signals 727 which are then fed into CRT monitor 735. How to carry out the transformation of the color coordinate converter from CIE-XYZ to RGB values is known in the art. The resulting image visualized on monitor 735 is a very accurate visualization of the overprint.

In another aspect of the present invention, the CIE-XYZ values 717, or the RGB values from lookup tables 725 may be fed to a multi-dimensional interpolator to determine the device dependent color values of a particular printing device such as a printer. The output of this interpolator can be sent to such a printing device. One practical application is color proofing, where the printing device is a proofing printer. The print resulting from such a printer is then an accurate simulation on the medium of the proofer of the overprint of the n colorants on the substrate of the profile. How to carry out color conversions from CIE-XYZ values or CIE-Lab values to the device color space of a particular printing device is known in the art.

In one preferred embodiment as a method for simulating the appearance of the overprint of the colorants on a printer, for example a proof printer, the simulation on a printer is a set of computer implemented method steps. These steps can be incorporated in a raster image processor ("RIP") system used to drive the printer.

As will be appreciated by those skilled in the art, embodiments of the present invention may be embodied as a method, an apparatus such as a special purpose apparatus, an apparatus such as a data processing system, or a carrier medium, e.g., a computer program product, carrier medium carrying one or more computer readable code segments for controlling a processing system to carry out a set of steps. Accordingly, the present invention may take the form of an entirely hardware embodiment, an entirely software embodiment or an embodiment combining software and hardware aspects. Furthermore, the present invention may take the form of carrier medium (e.g., a computer program product on a computer-readable storage medium) carrying computer-readable program code segments embodied in the medium. Any suitable computer readable medium may be used including a magnetic storage device such as a diskette or a hard disk, or an optical storage device such as a CD-ROM.

It will be understood that the steps of methods and flowcharts discussed are performed in one embodiment by an appropriate one or more processor of a processing (i.e., computer) system executing instructions (code segments) stored in storage. It will also be understood that the invention is not limited to any particular implementation or programming technique and that the invention may be implemented using any appropriate techniques for implementing the functionality described herein. The invention is not limited to any particular programming language or operating system.

The instructions (e.g., computer readable code segments in storage) may be read from storage into memory. Execution of sequences of instructions contained in memory causes one or more processor to perform the process steps described herein. In alternative embodiments, hard-wired circuitry may be used in place of or in combination with software instructions to implement the invention. Thus, embodiments of the invention are not limited to any specific combination of hardware circuitry and software.

The terms "carrier medium" and "computer-readable medium" as used herein refer to any medium that participates in providing instructions to a processor for execution. Such a medium may take many forms, including but not limited to, non-volatile media, volatile media, and transmission media. Non-volatile media includes, for example, optical or magnetic disks, such as a storage device which is part of mass storage. Volatile media includes dynamic memory such as RAM. Transmission media include coaxial cables, copper wire and fiber optics, including the wires that comprise a bus within a computer. Transmission media can also take the form of acoustic or light waves, such as those generated during radio wave and infra-red data communications.

Common forms of computer-readable media include, for example a floppy disk, a flexible disk, a hard disk, magnetic tape, or any other magnetic medium, a CD-ROM, any other optical medium, punch cards, paper tapes, any other physical medium with patterns of holes, a RAM, a PROM, an EPROM, a FLASH-EPROM, any other memory chip or cartridge, a carrier wave as described hereafter, or any other medium from which a computer can read.

Various forms of computer readable media may be involved in carrying one or more sequences of one or more instructions to a processor for execution. For example, the instructions may initially be carried on a magnetic disk of a remote computer. The remote computer can load the instructions into its dynamic memory and send the instructions over a telephone line using a modem. A modem local to the computer system can receive the data on the telephone line and use an infrared transmitter to convert the data to an infra-red signal. An infra-red detector coupled to a bus can receive the data carried in the infra-red signal and place the data on the bus. The bus carries data to main memory, from which a processor retrieves and executes the instructions. The instructions received by main memory may optionally be stored on a storage device either before or after execution by a processor. The instructions can also be transmitted via a carrier wave in a network, such as a LAN, a WAN, or the Internet.

While in one embodiment, the database contains colorant parameters for many different versions of each of C, M, Y and K, a best match is searched for each of C, M, Y, and K, and then the best database match colorant parameters are iteratively modified to provide a better match, in another embodiment, the database includes the colorant parameters of each of a single "typical" cyan, magenta, yellow, and black, and these typical CMYK parameters form the initial values for the iterative colorant parameters match. The typical parameters may be formed, for example, as the average colorant parameters for a collection of each of C, M, Y, and K.

Although device profiles in the description above provide colorimetric values in CE Lab, other profiles may be in some other color space, e.g., the CIE XYZ device independent color space, some modified RGB device independent color space, and so forth, and how to modify the embodiments to handle such other spaces would be clear to one in the art. Furthermore, while the colorant parameters, spectra, etc., are described as a function of wavelength, such spectral quantities may be provided as functions of frequency, and how to modify the embodiments to handle such data would also be clear to one in the art.

Although device profiles in the description above uses CMY and K as the device profile colorants, the invention is not limited to device profiles in terms of C,M, Y, and K, and how to modify the details to accommodate other device profile colorants would be straightforward and clear to those in the art.

While the examples above of determining the color of an overprint is of colorants that include one set of colorants for which a device profile is provided, and other colorants, the invention also is applicable to the case of the colorants including more than one set of colorants with a device profile for each set.

Note that some of the embodiments include determining the reflection spectrum that produces a provided CIE defined color. It may be, mathematically speaking, not possible to uniquely determine the reflection spectrum that produces the CIE defined color. In one embodiment, the spectrum is defined at 36 wavelengths, and thus consists of 36 numbers. If it is required for the color of this spectrum to match a predefined color, there are only three equations available to determine the 36 numbers. Some approximation is required. In practice, however not many feasible colorant spectra would match a provided color. In G. D. Finlayson and P. M. Morovic, "Cross Over Wavelengths of Natural Metamers," *Color Image Science* 2000, University of Derby, Apr. 10–12, 2000, it is shown that the spectra of metameric colors need to cross at certain wavelengths. Chances are low that natural dyes, having the same color when seen under a particular illuminant, are actually also doing this, without these dyes being the same. Indeed the number of possible dyes that are used to make a colorant is rather limited and therefore if the color of a colorant is known, the spectrum and the colorant properties are also known with a quite high probability.

For coverage percentages for which there is no data available in the device profile, in one embodiment, interpolation is used to determine the parameters for such coverage percentages.

There have been described herein what are believed to be the preferred embodiments of the invention. Those skilled in the art will recognize that other and further modifications may be made thereto without departing from the spirit of the invention, and it is intended to claim all such changes and modifications as fall within the scope of the invention.

What is claimed is:

1. A method to predict a color of an overprint of a set of colorants at a set of respective coverage percentages on a substrate of a substrate type using a printing technique, the method comprising the steps of:
    providing one or more device profiles for one or more subsets of the set of colorants for printing on the substrate with the printing technique;
    determining a first set of colorant parameters of the device profile colorants of the subsets;
    determining a spectrum of the substrate;
    providing a second set of colorant parameters of non-device profile colorants;
    determining the color of the overprint from said first and second colorant parameters, wherein said first and second sets of colorant parameters characterize said colorants as a function of at least a coverage percentage and a wavelength; and
    modifying data of the one or more device profiles such that the colorant parameters determined in the step of determining colorant parameters determines the colorant parameters of modified colorants that match a color of the respective device profile colorants and that cover at least a gamut of the respective device profiles.

2. A method as recited in claim 1, wherein the step of determining the color of the overprint includes determining coverage percentages of the modified colorants corresponding to the colorants of each subset, and using the coverage percentages of the modified colorants to determine the color of the overprint.

3. A method to predict the color of an overprint of a set of colorants at a set of respective coverage percentages on a substrate of a substrate type using a printing technique, the method comprising the steps of:
    providing one or more device profiles for one or more subsets of the set of colorants for printing on the substrate with the printing technique;
    determining the colorant parameters of the device profile colorants of the subsets;
    determining the spectrum of the substrate;
    providing the colorant parameters of the non-device profile colorants;
    determining the color of the overprint; and
    modifying data of the one or more device profiles such that the colorant parameters determined in the step of determining colorant parameters determines the colorant parameters of modified colorants that match a color of the respective device profile colorants and that cover at least a gamut of the respective device profiles.

4. The method of claim 1, wherein the step of determining the color of the overprint includes determining coverage percentages of the modified colorants corresponding to the colorants of each subset, and using the coverage percentages of the modified colorants to determine the color of the overprint.

* * * * *